(12) United States Patent
Kim

(10) Patent No.: US 11,951,308 B2
(45) Date of Patent: Apr. 9, 2024

(54) APPARATUS AND METHOD FOR TRANSORAL MINIMALLY INVASIVE TREATMENT OF GASTROINTESTINAL DISEASES

(71) Applicant: Daniel H. Kim, Houston, TX (US)

(72) Inventor: Daniel H. Kim, Houston, TX (US)

( * ) Notice: Subject to any disclaimer, the term of this patent is extended or adjusted under 35 U.S.C. 154(b) by 304 days.

(21) Appl. No.: 17/285,347

(22) PCT Filed: Feb. 19, 2019

(86) PCT No.: PCT/US2019/018627
§ 371 (c)(1),
(2) Date: Apr. 14, 2021

(87) PCT Pub. No.: WO2020/086110
PCT Pub. Date: Apr. 30, 2020

(65) Prior Publication Data
US 2021/0322769 A1   Oct. 21, 2021

Related U.S. Application Data

(60) Provisional application No. 62/751,206, filed on Oct. 26, 2018.

(51) Int. Cl.
*A61N 1/36* (2006.01)
*A61N 1/05* (2006.01)
*A61N 1/375* (2006.01)
*A61N 5/06* (2006.01)

(52) U.S. Cl.
CPC ....... *A61N 1/36007* (2013.01); *A61N 1/0517* (2013.01); *A61N 1/36085* (2013.01); *A61N 1/375* (2013.01); *A61N 5/0603* (2013.01); *A61N 2005/0609* (2013.01)

(58) Field of Classification Search
CPC .............. A61N 1/36007; A61N 1/0517; A61N 1/36085; A61N 1/375; A61N 5/0603; A61N 2005/0609
See application file for complete search history.

(56) References Cited

U.S. PATENT DOCUMENTS

| | | | | |
|---|---|---|---|---|
| 2004/0049181 | A1* | 3/2004 | Stewart | A61B 18/1492 606/41 |
| 2008/0015618 | A1* | 1/2008 | Sonnenschein | A61F 5/0086 606/157 |
| 2013/0090551 | A1* | 4/2013 | Sharma | A61N 1/0509 600/104 |

* cited by examiner

*Primary Examiner* — Tammie K Marlen
(74) *Attorney, Agent, or Firm* — NZ CARR LAW OFFICE

(57) ABSTRACT

Provided herein as a transoral minimally invasive method and a system thereof for the treatment of gastrointestinal diseases and/or obesity, which at least partially encircles a part of the gastrointestinal tract, such as esophagus of the patient by advancing an elongated deformable portion of a neurostimulator assembly endoluminally to the subfascial area from the outer wall of the esophagus and introducing the elongated deformable portion sub-fascially in the sub-fascial area, whereby at least one part of the encircled esophagus will be modulated using a modulator.

13 Claims, 14 Drawing Sheets

APPARATUS AND METHOD FOR TRANSORAL MINIMALLY INVASIVE TREATMENT OF GASTROINTESTINAL DISEASES

CROSS REFERENCE TO RELATED APPLICATION

This application is a National Stage Application of International Application No. PCT/US2019/018627, filed on Feb. 19, 2019, which claims benefit of U.S. Provisional Application Ser. No. 62/751,206, filed Oct. 26, 2018, entitled "APPARATUS AND METHOD FOR TRANSORAL MINIMALLY INVASIVE TREATMENT OF GASTROINTESTINAL DISEASES," which is incorporated herein by reference in its entirety

BACKGROUND

Field

The present specification relates to surgical apparatuses, systems and procedures used for minimally invasive surgery. More specifically, the present specification relates to the field of surgical apparatuses, systems and procedures useful for use in transoral or endoluminal treatment of gastrointestinal diseases and/or obesity.

Description of the Related Art

Gastrointestinal diseases refer to diseases involving the gastrointestinal tract, namely the esophagus, stomach, small intestine, large intestine and rectum, and the accessory organs of digestion, the liver, gallbladder, and pancreas, including such conditions as gastroesophageal reflux, abdominal pain, constipation, irritable bowel syndrome, hemorrhoids, anal fissures, perianal abscesses, anal fistulas, perianal infections, diverticular diseases, colitis, colon polyps and cancer.

Gastroesophageal reflux disease (GERD) is the most common gastrointestinal disease of the esophagus. It is a chronic, progressive disorder that presents most typically with heartburn and regurgitation and atypically with chest pain, dysphagia, chronic cough, globus, or sore throat. The mainstay for diagnosis and characterization of the disorder is esophagoduodenoscopy (EGD), high-resolution esophageal manometry, and symptom-associated ambulatory esophageal pH impedance monitoring. Epidemiological data have demonstrated that obesity is an important risk factor for the development of gastroesophageal reflux disease. There is also accumulating data that obesity is associated with complications related to longstanding reflux such as erosive esophagitis, Barrett's Esophagus, and esophageal adenocarcinoma.

Treatment regimens for GERD have included various dietary and lifestyle modifications (such as avoidance of acidic foods, carbonated beverages, alcohol, and tobacco), as well as pharmaceutical compositions (e.g. anti-secretory drugs, most commonly proton pump inhibitors (PPIs)) and surgery. Numerous surgical procedures for the treatment of GERD are known in the prior art. One surgical approach to GERD treatment is Laparoscopic Fundoplication, which is a minimally invasive procedure done to restore the function of the lower esophageal sphincter (the valve between the esophagus and the stomach) by wrapping the stomach around the esophagus, so that a new "functional valve" between the esophagus and the stomach and prevents reflux of the acid and bile (non-acidic fluid) from the stomach into the esophagus.

Another approach to the treatment of GERD is gastric bypass surgery, which is a type of weight-loss surgery that involves creating a small pouch from the stomach and connecting the newly created pouch directly to the small intestine, leading to decreased nutrient absorption by the patient and symptom alleviation of GERD. A further approach is the application of magnetic sphincter augmentation, which is designed to augment the lower esophageal sphincter (LES) through magnetomechanical means (such as The Linx™ Reflux Management System (Torax Medical, Shoreview, Minn.), consisting of magnetic beads that are connected by titanium links that allow the beads to open during a swallow or belch. The force of magnetic attraction exerts forces to strengthen the LES.). Yet another approach is Electrical Stimulation laparoscopically implanting electrodes in the LES (EndoStim LES Stimulation System; EndoStim BV, The Hague, The Netherlands), which automatically delivers tiny electronic pulses from the implanted pulse generator to the weak LES muscle. The pulses stimulate the muscle to function as a healthy LES, opening for swallowing, belching, and other normal behaviors, but remaining closed at other times.

Additionally, several technologies have been developed to offer transoral minimally invasive methods for treatment of GERD. The procedures are typically performed endoscopically under general anesthesia. The Esophyx® device (Endogastric Solutions, Redmond, Wash.) claims to restore the dynamics of the angle of the gastroesophageal valve (GEV), to help restore the GEV's function as a reflux barrier by endoscopically deploying a greater than 270° internal wrap or fundoplication. The device utilizes a tissue grasping mechanism and proprietary stapling system that is passed over a standard endoscope. In contrast to the Esophyx® device, the MUSE™ system (Medigus, Israel) is an ultrasonic surgical stapler embedded within a custom endoscope to perform a similar transoral fundoplication The procedures outlined above have been limited by various factors. For example, the patients of Laparoscopic Fundoplication require hospitalization for this procedure and a seven to ten-day recovery period. Also, various gastric bypass procedures, in which a portion of the gastro-intestinal tract is surgically excised, have led to under-nourished or malnourished patients, and furthermore such procedures are typically highly invasive and irreversible. Further, the use of magnetic sphincter augmentation has been explored only for small hiatal hernias where a primary crural repair is performed concurrently. Additionally, the Linx™ system, which employs a plurality of titanium beads with magnetic cores, is used to treat GERD. However, the Linx™ system is incompatible with magnetic resonance imaging (MRI).

As can be seen, there is a need for apparatuses, systems, and methods for the safe, reliable, cost-effective, and minimally invasive treatment of gastrointestinal diseases and/or obesity.

SUMMARY

The present invention provides systems, apparatus, and methods for the effective and minimally invasive treatment of gastrointestinal diseases (such as gastro-esophageal reflux disease (GERD)) and/or obesity. In an embodiment the invention provides a transoral minimally invasive method and implantable device for treatment of the patient. The device is adjustable (e.g., deformable, bendable or expandable) in at least one dimension to partially encircle one or more tissues or organs targeted for treatment for exerting of a suitable stimulation (such as mechanical force or electrical force) thereon.

According to the present invention, a transoral minimally invasive method for treating a patient is provided herein, comprising: a) placing an endoscopic device endoluminally with respect to esophagus of the patient to a first targeted site within esophagus, wherein said endoscopic device includes: a flexible insertion tube having a proximal end and a distal end and configured for extending in a longitudinal direction and be inserted into a body lumen; an ultrasound transducer provided at the distal end and configured for emitting ultrasound and producing ultrasound data to navigate the distal end of the insertion tube to the first targeted site and; a first working channel provided at the distal end and configured for slidingly providing tool access and control; b) inserting a flexible, elongated member with a piercing member at the distal end thereof through the first working channel to the first targeted site; c) creating a connected channel between an inner wall and an outer wall of esophagus by perforating the inner wall at the first targeted site to the outer wall thereof with the piercing member; d) introducing a neurostimulator assembly comprising a flexible sheath and a steerable guide member therein through the first working channel, the connected channel to the outer wall of esophagus, wherein said guide member comprising: an elongated deformable portion at a distal end of the guide member, and at least one modulator being deployed about an exterior surface of the elongated deformable portion; and e) at least partially encircling the esophagus of the patient with the modulator by advancing the elongated deformable portion of said guide member sub-fascially in a subfascial area from the outer wall of the esophagus.

In one embodiment, the endoscopic device of the step a) may further comprise an imagining device, illuminating device or one or more additional working channels, which can be provided at the distal end.

In one embodiment, the first targeted site of the step b) may be located at the esophagogastric junction, the esophageal-diaphragmatic junction, or the gastro-diaphragmatic junction but not limited to this.

In one embodiment, the step b) may further comprise: placing a balloon catheter having at least an inflatable balloon to the esophagogastric junction, so that the inner wall of the esophagus can be supported and kept in the original shape to facilitate the perforation of the piercing part when the balloon is inflated. Also, the encircled elongated deformable portion can be maintained at a predetermined position without sliding away with the help of the inflated balloon.

In one embodiment, the elongated deformable portion of the step d) may further comprise a curved portion, whereby a distal end of the elongated deformable portion is guided through the curved portion to encircle the esophagus. In another embodiment, the distal end of the elongated deformable portion may be secured via any mechanical means known in the art (such as hooks or plug-and-socket type connectors, but not limited to this) to the proximal end.

In one embodiment, the step e) may further comprise applying a magnetic force to guide the elongated deformable portion of the guide member. For example, the elongated deformable portion of the guide member may further comprise a magnetic proximal end, so that the distal end of the elongated deformable portion can be guided by the magnetic force to encircle the esophagus.

In one embodiment, the guide member of the step d) may further comprise an inflatable balloon area at the distal end of the guide member, so that the subfascial area can be opened up or dissected and facilitate the advancement of the elongated deformable portion when the balloon area is inflated.

In one embodiment, the modulator may be any type of modulators, for example, comprising a device selected from the group consisting of monopolar electrodes, bipolar electrodes, quadrapolar electrodes, multipolar electrodes, optical stimulation devices, electromagnetic stimulation devices, radiofrequency stimulation devices, electrostatic stimulation devices, magnetic stimulation coils, vibratory stimulation devices, mechanical stimulation devices, acoustic stimulation devices, drug delivery catheters, chemical stimulation devices, electrolytic stimulation devices, thermal stimulation devices, neural stimulation devices, neural inhibition devices or the like.

In an embodiment, the modulator can be used to perform a modulating step by, for example, applying a stimulation selected from mechanical, optical, electromagnetic (such as radiofrequency), thermal, cold, electrical, magnetic, chemical, acoustic, pharmaceutical stimulation or the combination thereof to targeted sensory or motor nerve tissue.

In one embodiment, the modulating step can be performed selectively in the targeted areas such as sympathetic afferent neurons, sympathetic efferent neurons, parasympathetic afferents, vagal nerve afferent fibers, gastric circular muscle layer fibers, locus ceruleus neurons, intermediolateral nucleus neurons, sympathetic trunk neurons, modulating splanchnic nerve neurons, but not limited to this. In other embodiments, at least one part of the encircled esophagus of the step e) to perform modulating, may be, for example but not limited to, a vagal nerve, the diaphragmatic muscle, splanchnic nerve or the celiac ganglia.

The present invention also provides a device for providing a transoral minimally invasive therapy to a patient, comprising: a flexible sheath having an interior, and a steerable guide member extending or retracting in the interior, wherein said guide member has a distal end and further comprises: an elongated deformable portion provided the distal end and at least one modulator being deployed about an exterior surface of the elongated deformable portion.

In one embodiment, the guide member may further comprise a curved portion configured for guiding a distal end of the elongated deformable portion. Also, the distal end of the sheath may further comprise a first connecting port (such as a hook-like structure or a plug), while the proximal end further may comprise a corresponding second port configured for securing with the first connecting port (such as a hook-like structure or a sock structure corresponding to the plug).

In one embodiment, the elongated deformable portion of the guide member may further comprise a magnetic proximal end and a corresponding magnetic distal end configured for guide the distal end to encircle the esophagus. In other embodiments, the guide member may further comprise an inflatable balloon area provided at the distal end of the guide member and configured for opening up the subfascial area when the balloon area is inflated.

In one embodiment, the elongated deformable portion is implantable. For example, the neurostimulator assembly may further include a generator. The generator may be implanted in the patient's body, such as in a pocket formed by the implanting surgeon just below the skin in the abdomen. The generator may be in electrical communication with the modulator of the elongated deformable portion via lead wires housed in the lead conduit. The generator may be operable to deliver a signal to at least one part (such as a vagal nerve, the diaphragmatic muscle, splanchnic nerve and/or the celiac ganglia) of the encircled esophagus, thereby stimulating the nerve and promoting a feeling of satiety. Alternatively, the generator may deliver the signal to the at least one part of the encircled esophagus to inhibit or block the nerve.

These and other features, aspects, and advantages of the present invention will become better understood with reference to the following drawings, description, and claims.

BRIEF DESCRIPTION OF THE DRAWINGS

FIG. 9-A is a schematic view of the neurostimulator assembly being placed in the subfascial area shown in FIG. 1C according to one embodiment, illustrating a joint-type guide member which forms a curved portion to guide the elongated deformable portion.

DETAILED DESCRIPTION

Figure 1A:
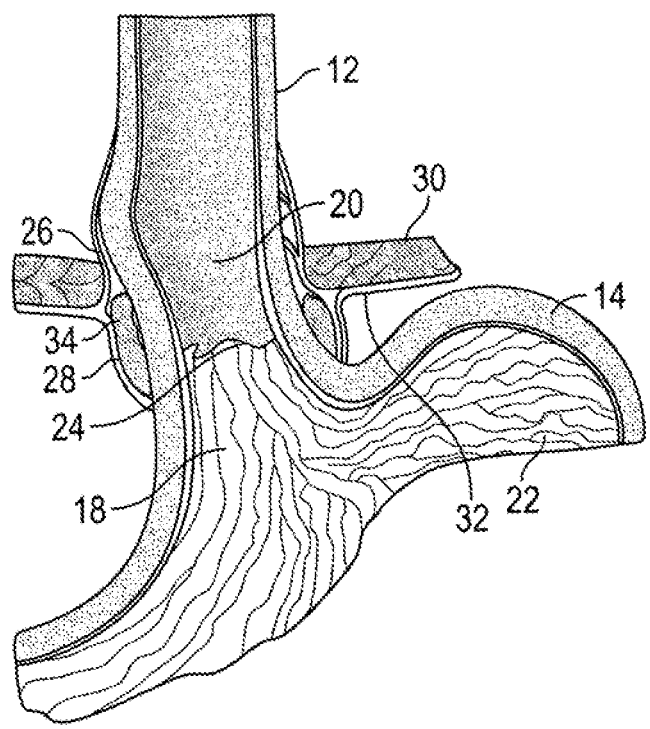
FIG. 1A is a view of a portion of a human gastro-intestinal (GI) tract.
Figure 1B:
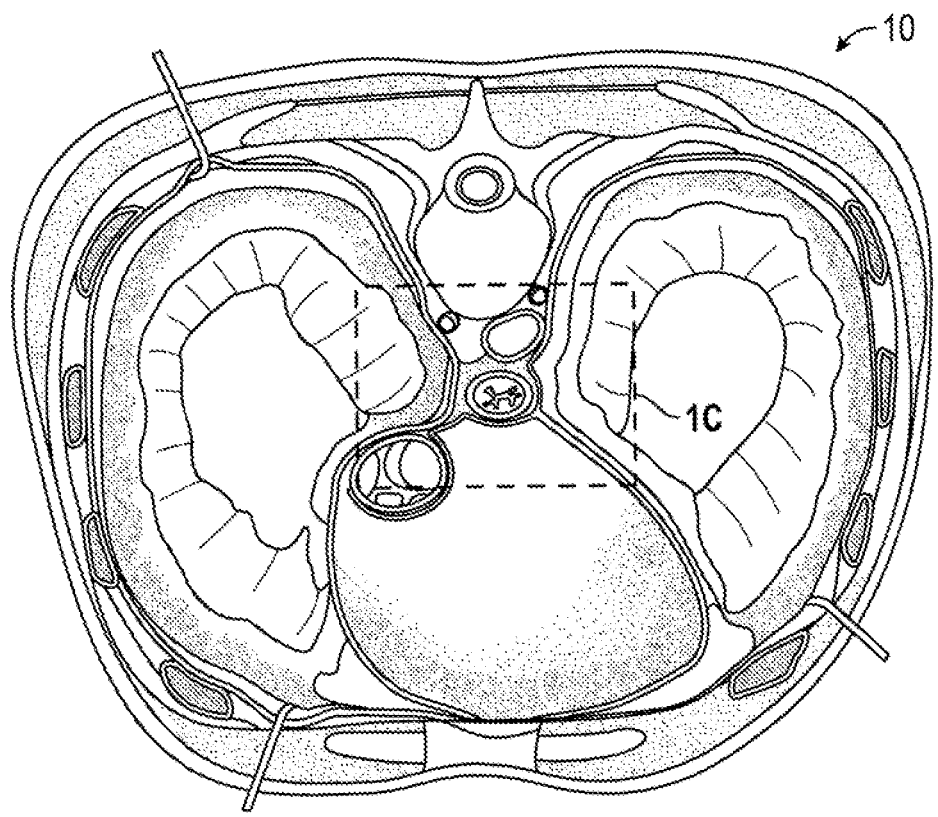
FIG. 1B is a cross section of the GI tract of FIG. 1A.
Figure 1C:
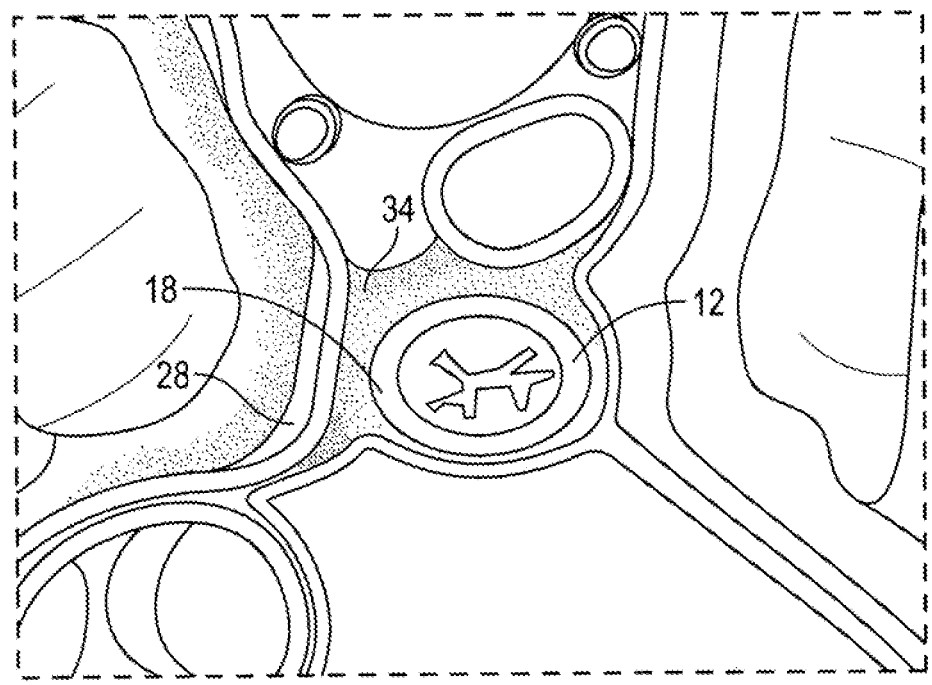
FIG. 1C is an enlarged view of FIG. 1B.

FIG. 1A hereof is a sectional view of a portion of a human gastro-intestinal (GI) tract 10 (hereafter, GI tract 10), such as that disclosed in U.S. Pat. Nos. 8,868,215 and 8,874,216, which are incorporated herein by reference in their entireties, except for any definitions, subject matter disclaimers or disavowals, and except to the extent that the incorporated material is inconsistent with the express disclosure herein, in which case the language in this disclosure controls. FIG. 1B is a cross section of the GI tract 10 of FIG. 1A. FIG. 1C is an enlarged view of a portion of the GI tract 10 of FIG. 1B. The GI tract 10 includes the esophagus 12, the stomach 14, the diaphragm 16, and the cardiac orifice 18. The histology change between esophageal tissue 20 of the esophagus 12 and the gastric tissue 22 of the stomach 14 occurs at esophagogastric junction 24, which is also called the "z-line". The esophagus 12 passes through an opening of the diaphragm 16 known as the esophageal hiatus 26. Proximately above the esophageal hiatus 26, the esophagus 12 is anchored to the diaphragm 16 by an upper limb of the phrenoesophageal ligament 28 (hereafter, POL 28). The POL 28 is formed from two closely applied layers including a layer derived from endothoracic fascia 30 and a layer derived from transversalis fascia 32. A lower limb of the POL 28 attaches to the stomach 14 proximately below the esophageal hiatus 26. A subfascial area 34 (i.e. gastroesophageal (GE) space) is formed between an inner wall of the POL 28 and outer wall of the esophagus 12 and of the cardiac orifice 18. The subfascial area 34 is filled with adipose tissue and is traversed by blood vessels.

Herein, a transoral minimally invasive method to place a neurostimulator assembly 100 endoluminally into the esophagus 12 interiorly of an intended placement location thereof around the esophagus 12, then through the inner wall 52 of the esophagus 12 and outwardly of the outer wall 86 thereof (see, e.g. FIG. 4), and into the subfascial area 34, and then introducing an implantable elongated deformable portion 54 (see, e.g. FIG. 8) of the neurostimulator assembly 100 sub-fascially in the subfascial area 34 to encircle or substantially encircle at least one part of the esophagus 12 so that the encircled or substantially encircled part of the esophagus 12 (such as a vagal nerve, the diaphragmatic muscle, splanchnic nerve and/or the celiac ganglia) can be modulated electrically and/or mechanically using the neuromodulator of the elongated deformable portion 54, is described and shown.

Figure 2:
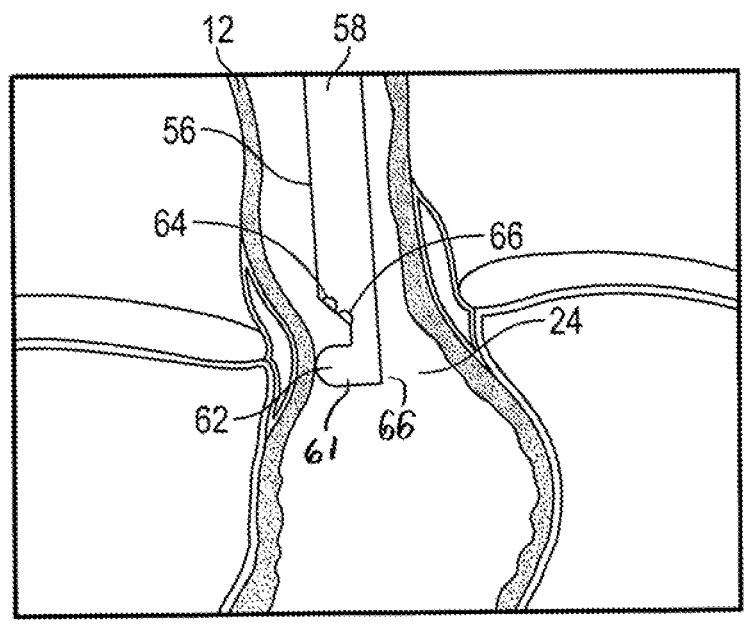
FIG. 2 is a schematic view, showing an esophagus in section, of one step of the transoral minimally invasive method according to one embodiment, illustrating endoscopic device introduced endoluminally with respect to esophagus of the patient to a targeted site within esophagus.

FIG. 2 is a schematic view of one step of the transoral minimally invasive method according to one embodiment hereof, illustrating an endoscopic device introduced endoluminally with respect to esophagus of the patient to a targeted site within esophagus. As shown in FIGS. 1, the endoscopic device is an ultrasound endoscope 56 placed with respect to the interior of the esophagus 12 of the patient at the esophagogastric junction 24. The ultrasound endoscope 56 can be any type known in the art, including, for example a device configured of: a flexible insertion tube 58 (partially shown) having a proximal end (not shown) and a distal end 60, the flexible insertion tube 58 configured for extending in a longitudinal direction and insertable into a body lumen, here the esophagus 12. The ultrasound flexible insertion tube 58 includes an ultrasound transducer 61 provided at the distal end 60 thereof, which is configured for emitting ultrasound (i.e., high frequency sound waves) and receiving reflected sound waves and thereby producing detailed images of the lining and walls of the esophagus 12. The ultrasound endoscope 56 comprises a handle (not shown) provided at the proximal of the flexible insertion tube 58. The handle includes a deflection control knob (not shown) which the operator moves to selectively and controllably bend the flexible insertion tube 58 at the distal end 60 thereof, so that an operator of the ultrasound endoscope 56 can navigate the distal end 60 of the flexible insertion tube 58 to a targeted site within the esophagus 12 based on detailed image thereof provided by the ultrasonic transducer 61 and endoscope 56. In an example, the distal end 60 of the flexible insertion tube 58 includes a camera 62, a first working channel 64 and one or more additional working channels 66 (66A, 66B) for slidingly providing tool access and control, an illuminating device (not shown) such as a LED or light bundle, as well as irrigation and suction ports (not shown), or inflatable devices such as one or more inflatable members such as balloons.

Figure 3A:
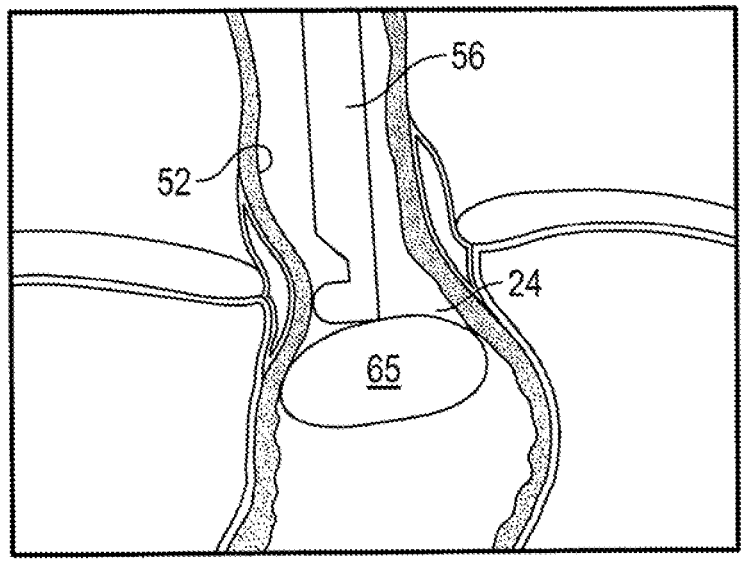
FIG. 3A is a schematic view, showing an esophagus in section, of one step of the transoral minimally invasive method according to one embodiment, illustrating single endoscope balloon insufflated at a targeted site of the esophagogastric junction.
Figure 3B:
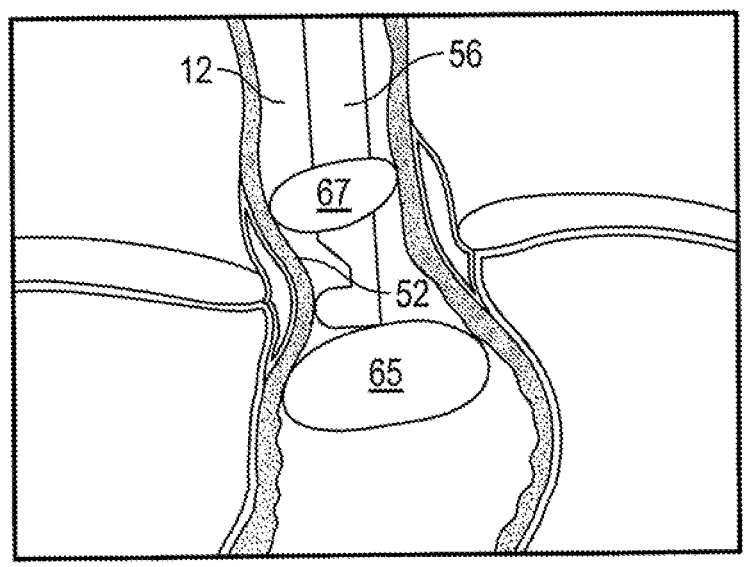
FIG. 3B is a schematic view, showing an esophagus in section, of one step of the transoral minimally invasive method according to another embodiment, illustrating double endoscope balloons insufflated at a targeted site of the esophagogastric junction.

FIGS. 3A and 3B are schematic views of one step of different variants of a portion of the transoral minimally invasive method according to one embodiment hereof, illustrating that a single endoscope balloon 65 (first balloon) is insufflated adjacent the targeted location of the esophagogastric junction 24. FIG. 3B is a schematic view of one step of the transoral minimally invasive method according to another embodiment, illustrating that two endoscope balloons 65, 67 are insufflated at the targeted site of the esophagogastric junction 24. As shown in FIG. 3B a balloon catheter (not shown) known in the art can be introduced through the second working channel (not shown) and used to deliver, and insufflate, the endoscope balloon 65 as shown in FIG. 3A. The balloon catheter, as known in the art, comprises a flexible, elongated catheter shaft having a bore, a guidewire extendable or retractable through the bore of the balloon catheter and an opening at the distal end thereof, and an inflatable balloon 65 (FIG. 2) provided at the distal end of the guidewire. In the variant shown in FIG. 3B, two inflatable balloons are delivered by two different balloon catheters (not shown), each balloon being provided at the distal end of a guidewire of a different one of the balloon catheters, wherein one balloon catheter is introduced through a second working channel and the other introduced through the additional working channel (not shown) B. In the embodiment shown in FIG. 3A, the single balloon 65 is deployed adjacent to the esophogastric junction 24 on the stomach 14 side thereof. In the embodiment shown in FIG. 3B, the balloon 65 is deployed adjacent to the esophogastric junction 24 on the stomach 14 side thereof, and a second balloon 67 is deployed through the additional working channel to surround or partially surround the ultrasound endoscope 56. When the distal end of the guidewire of the balloon catheter(s) is extended and positioned adjacent the esophagogastric junction 24, the balloon 65(s) is inflated, and the balloon catheter removed. In the embodiment of FIG. 3B, two balloon catheters, one in each of the second working channels 66A, 66B, are deployed and the balloon catheters removed. The inner wall 52 of the esophagus 12 can be supported by the inflated balloon and kept in its original shape to facilitate the local perforation thereof (the details will be discussed below). Also, the balloon(s) 65, 67, when inflated, stabilize the distal end 60 portion of the ultrasound endoscope 56, thereby enabling placement and maintenance of an encircling elongated deformable portion 54 of the neurostimulator assembly 50 during deployment thereof to surround the esophagus 12.

Figure 4:
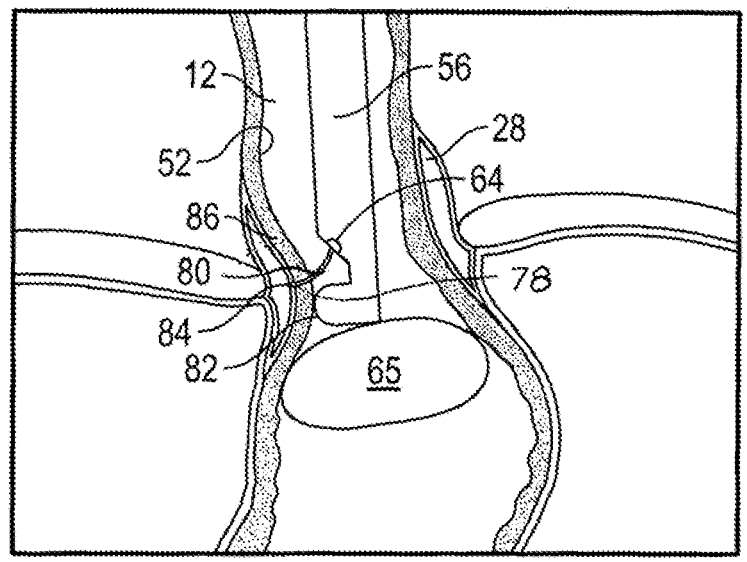
FIG. 4 is a schematic view, showing an esophagus in section, of one step of the transoral minimally invasive method according to one embodiment, illustrating a puncturing device introduced to the targeted site to create a connected channel between the interior of the esophagus and the subfascial area of the phrenoesophageal ligament (POL).
Figure 17:
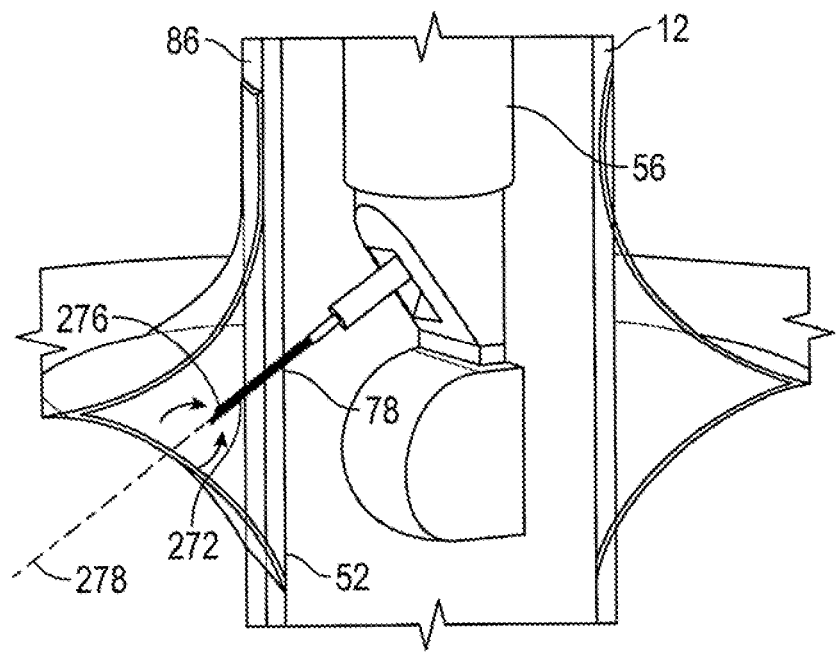
FIG. 17 an isometric view of the portion of the esophagus of FIG. 15, showing an anchor penetrating through the wall of the esophagus and into the subfascial region thereabout.

FIG. 4 is a schematic view of one step of the transoral minimally invasive method according to one embodiment, illustrating a single insufflated balloon 65 deployed adjacent the esophogogastric junction 24, and the extension of a puncturing device 78 from the first working channel 64 of the ultrasound endoscope 56 toward, into, and through the structure of the esophagus 12 at the targeted site at the inner wall 52 of the esophagus 12, to create an opening through the structure of the esophagus 12 from and through the inner and outer walls 52, 86 thereof, forming the connected channel 78 to extend between the interior of the esophagus 12 and the subfascial area 34 of the POL 28. The puncturing device 80 includes a flexible, elongated member 82, with a piercing part 84 at its distal end. In an example, the puncturing device is a needle, a cannula or an ablation catheter. Once the piercing part 84 reaches the targeted site at the esophagogastric junction, the local inner wall 52 and outer wall 86 of esophagus 12 are perforated by the piercing unit 84 pushing into the inner wall 52 of the esophagus as a result of mechanical force being applied thereat though the piercing part 84 (e.g. a needle tip or a cannula tip) or with an anchor (FIG. 17). Alternatively, the inner wall 52 and the outer wall 86 of esophagus 12 can be perforated by thermal or cryo-energy applied though a piercing part 84 (e.g. a tip of the ablation catheter). Thus, the connected channel 78 is created connecting the interior volume of the esophagus with the subfascial area 34 of the POL 28.

Figure 5:
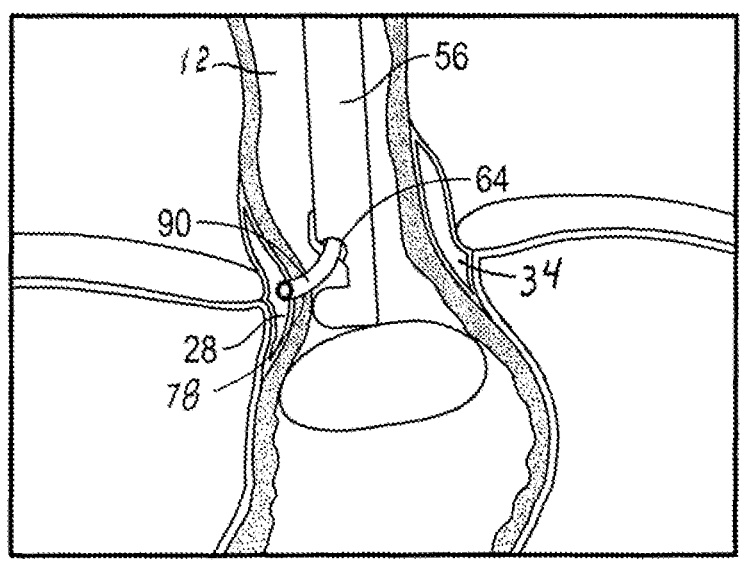
FIG. 5 is a schematic view, showing an esophagus in section, of one step of the transoral minimally invasive method according to one embodiment, illustrating a flexible sheath of a neurostimulator assembly introduced to the targeted subfascial area of POL through the connected channel.
Figure 6:
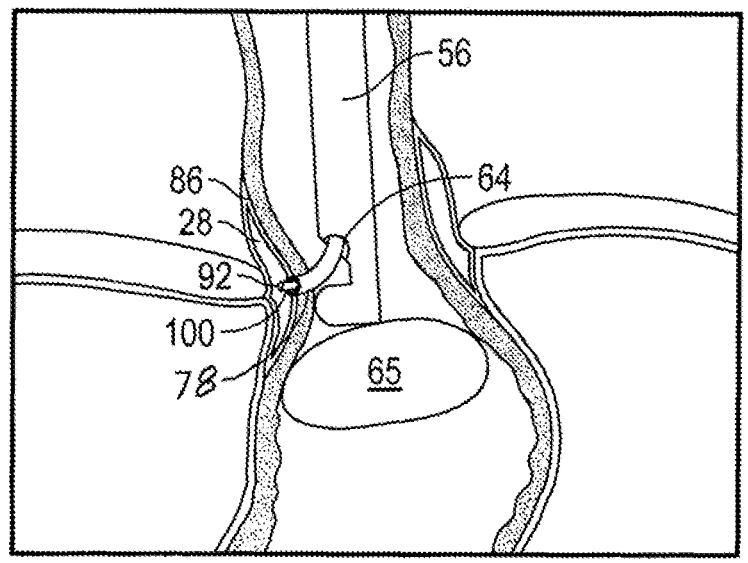
FIG. 6 is a schematic view, showing an esophagus in section, of one step of the transoral minimally invasive method according to one embodiment, illustrating a guide member of a neurostimulator assembly advanced within a flexible sheath to the targeted subfascial area of POL through the connected channel.

FIG. 5 is a schematic view of one step of the transoral minimally invasive method according to one embodiment, illustrating that a flexible elongated sheath 90 of a neurostimulator assembly is introduced through the connected channel 78 extending though the structure of the esophagus 12 and to the targeted subfascial area 34 of the POL 28. FIG. 6 is a schematic view of one step of the transoral minimally invasive method according to one embodiment, illustrating a guide member 92 for guiding a neurostimulator assembly 100 (FIGS. 6 to 8) advanced within the flexible sheath 90 to the targeted subfascial area 34 of the POL 28. In an example, the neurostimulator assembly 100 comprises the flexible, elongated sheath 90 having an interior and a steerable guide member extending or retracting inwardly and outwardly of the interior (see, e.g. FIGS. 6 to 8). The flexible, elongated sheath 90 is introduced into the first channel 64 of the ultrasound endoscope and thence through the connected channel 78 to the targeted subfascial area 34 of the POL 28. Then, the guide member 92 is advanced within the flexible elongated sheath 90 and outwardly of the outer wall 86 of esophagus 12 and thereby reaches the targeted subfascial area of the POL 28.

Figure 7A:
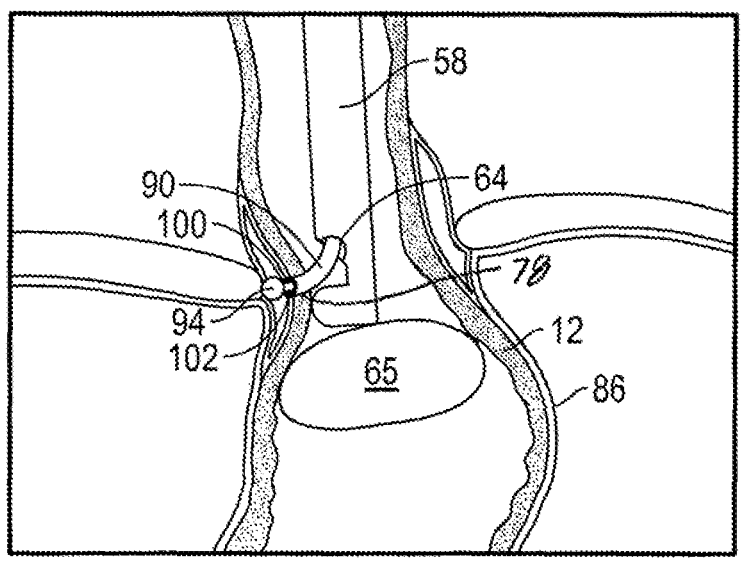
FIG. 7A is a schematic view, showing an esophagus in section, of one step of the transoral minimally invasive method according to one embodiment, illustrating an attached balloon at a distal end of an elongated deformable portion of a guide member insufflated in the targeted subfascial area of POL.
Figure 7B:
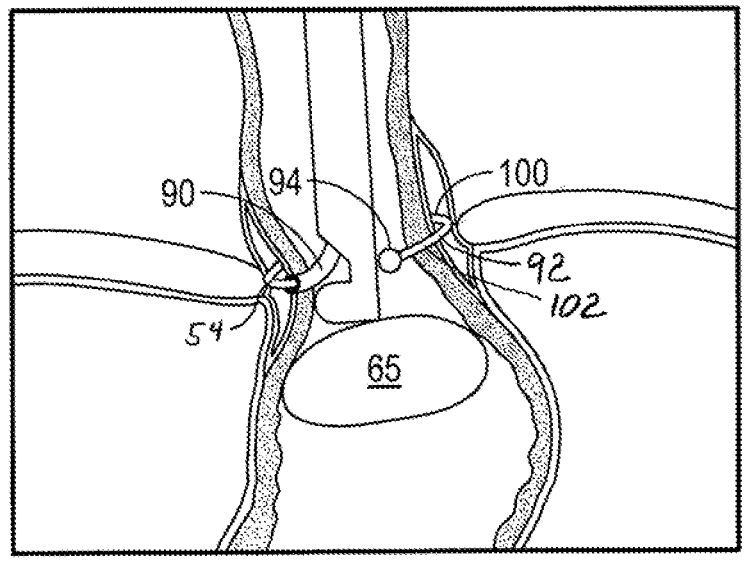
FIG. 7B is a schematic view, showing an esophagus in section, of one step of the transoral minimally invasive method according to one embodiment, illustrating the elongated deformable portion of the guide member advanced sub-fascially in a subfascial area to at least partially encircling the esophagus of the patient.
Figure 8:
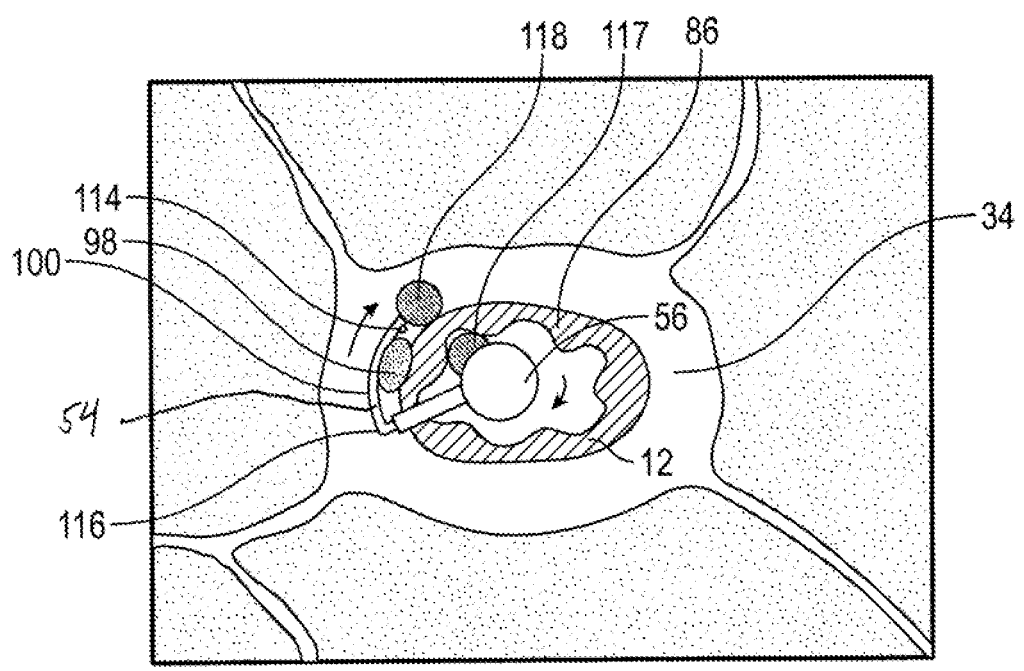
FIG. 8 is a schematic view, showing an esophagus in section, of the neurostimulator assembly being placed in the subfascial area shown in FIG. 1C according to one embodiment, illustrating a magnet-type elongated deformable portion of a guide member comprising a magnetic distal end, with a corresponding magnet, being placed within the lumen of the esophagus.

FIG. 7A is a schematic view of one step of the transoral minimally invasive method according to one embodiment, illustrating a guide balloon 94 attached at the distal end of an elongated deformable portion of a guide member, here the distal end of the guide member 92 extending from the flexible elongated sheath 90, insufflated within the targeted region of the subfascial area 34 of the POL 28. In FIG. 7B, a schematic view of one step of the transoral minimally invasive method according to one embodiment, the guide balloon 94 on the distal end of the guide member 92, and the elongated deformable portion 54 of the guide member 92 have been advanced from the ultrasound endoscope 56 through the connected channel 78 through the physical mass of the esophagus, and thereby deployed sub-fascially in the sub fascial 34 area to at least partially encircle the esophagus 12 of the patient. In FIG. 7B, the guide member 92 of the neurostimulator assembly 100 comprises an elongated deformable portion 102 at a distal end of the guide member 92 having at least one modulator 104 (see, e.g. FIG. 10A) being deployed about an exterior surface of the elongated deformable portion. In an example, the elongated deformable portion 102 comprises: a shape-memory wire or strap 116 with the balloon 94 attached to the distal end of the shape-memory wire or strap (see, e.g. FIG. 7A). In another example as illustrated in FIG. 8, the elongated deformable portion 54 comprises: a shape-memory wire or strap 116 having an inflatable balloon area 98 formed within its distal end and a first magnet 118 provided at the distal end of the inflatable balloon area. (see, e.g. FIG. 7-1). The attached balloon 94 or the inflatable balloon area 98 is insufflated by any current technologies known in the art, such as the balloon techniques discloses in U.S. Pat. No. 8,868,215 B2, which are incorporated herein by reference in their entireties, except for any definitions, subject matter disclaimers or disavowals, and except to the extent that the incorporated material is inconsistent with the express disclosure herein, in which case the language in this disclosure controls. As also shown in FIG. 8 a second magnet 117 is mounted on the ultrasound endoscope 56, and this magnet rotates as the endoscope rotates to deploy the neurostimulator assembly 100, which attracts magnet 118 thereby pulling the neurostimulator assembly close to the outer wall 86 of the esophagus 12.

Referring to FIGS. 7A and 8, when the distal end of the elongated deformable portion 54 of the guide member 92 is introduced into the subfascial area 34, the insufflated balloon 94 or the inflatable balloon area 98 thereof can help to open up or dissect the subfascial area 34 and thereby facilitate the advancement of the elongated deformable portion 54 circumferentially about the outer wall 86 of the esophagus 12. Thus, at least one part or portion of the esophagus 12 is partially or fully encircled by the elongated deformable portion 54 as shown in FIG. 10A. Then, modulation can be performed on the targeted treatment area (e.g. vagal nerves, diaphragmatic muscles, splanchnic nerves, the celiac ganglia or the combination thereof) of the encircled portion of the esophagus using the modulator 104 of the neurostimulator assembly 100. The modulation can be performed by applying suitable stimulation to the targeted area such as mechanical, optical, electromagnetic (such as radiofrequency), thermal, cold, electrical, magnetic, chemical, acoustic or pharmaceutical stimulation, but not limited to this. Herein, neuromodulation, either by blocking or stimulating transmission of neural impulses, is induced electrically via application of electrical signals to the targeted treatment area through the wire of the neurotransmitter assembly 100 and thence the modulator 104, or mechanically by exertion of a suitable mechanical force caused by the elongated deformable portion on the targeted treatment area by mechanical leverage against the POL 28 tending to bend the end of the wire toward the esophagus 12 (e.g. by inflation of the balloon area in FIG. 8 or the attached balloon in FIG. 9A to mechanically reinforce the targeted area). The electrical or mechanical modulation can reinforce the muscular layers of the esophagus 12, or mechanically reinforce the lower esophageal sphincter of the patient, thereby tightening the lower esophageal sphincter, thereby decreasing or preventing gastric reflux and effectively treats GERD.

FIG. 8 is a schematic view of the neurostimulator assembly being placed in the subfascial area shown in FIG. 1C according to one embodiment, illustrating a magnet-type elongated deformable portion of a guide member comprising a magnetic distal end, while a corresponding magnet (not shown) is placed within the lumen of the esophagus 12. As shown in FIGS. 8 to 10A, the distal end of the elongated deformable portion 54 comprises at least one neuromodulator 114 being deployed on an exterior surface of the elongated deformable portion 92. The neuromodulator can be any devices known in the art, such as monopolar electrodes, bipolar electrodes, quadrapolar electrodes, multipolar electrodes, optical stimulation devices, electromagnetic stimulation devices, radiofrequency stimulation devices, electrostatic stimulation devices, magnetic stimulation coils, vibratory stimulation devices, mechanical stimulation devices, acoustic stimulation devices, drug delivery catheters, chemical stimulation devices, electrolytic stimulation devices, thermal stimulation devices, neural stimulation devices, neural inhibition devices, or the like. Herein, the modulator comprises at least one electrode. Also, the magnet-type elongated deformable portion 54 of the guide member comprises a magnetic distal end (i.e. a first magnet 118), while a corresponding second magnet 117 can be placed within the lumen of the esophagus as shown in FIG. 8 (for example, one of additional working channels 66 of the ultrasound endoscope 56 in FIG. 2). In this way, the operator can selectively and controllably use the handle (not shown) of the endoscope to rotate the endoscope 56 so that the second magnet 117 within the additional working channel 66 of the endoscope 56 can rotate accordingly. Then, magnetic attraction formed between the first magnet 118 and the second magnet 117 will guide the first magnet 118 to move within the sub-fascial area 34 in relative to the outer wall 86 of the esophagus 12. Thus the elongated deformable portion 54 can be guided by the first magnet 118 to partially or fully encircle the esophagus 12.

Additionally, the elongated deformable portion 54 of FIG. 8—can be designed as an implantable device using the current technologies known in the art, such as the generator discloses in the U.S. Pat. No. 8,868,215 B2, which is incorporated herein by reference in the entireties, except for any definitions, subject matter disclaimers or disavowals, and except to the extent that the incorporated material is inconsistent with the express disclosure herein, in which case the language in this disclosure controls. For example, an implantable pulse generator may be implanted in the patient's body, such as in a pocket formed by the implanting surgeon just below the skin in the abdomen. The generator has at least a lead wire electrically connected to the modulator. Alternatively, the generator may include only a housing, an antenna, a receiver, and an RF generator and deliver the signal to the electrodes when powered wirelessly, analogously to a passive RFID tag.

Figures 9A, 9B:
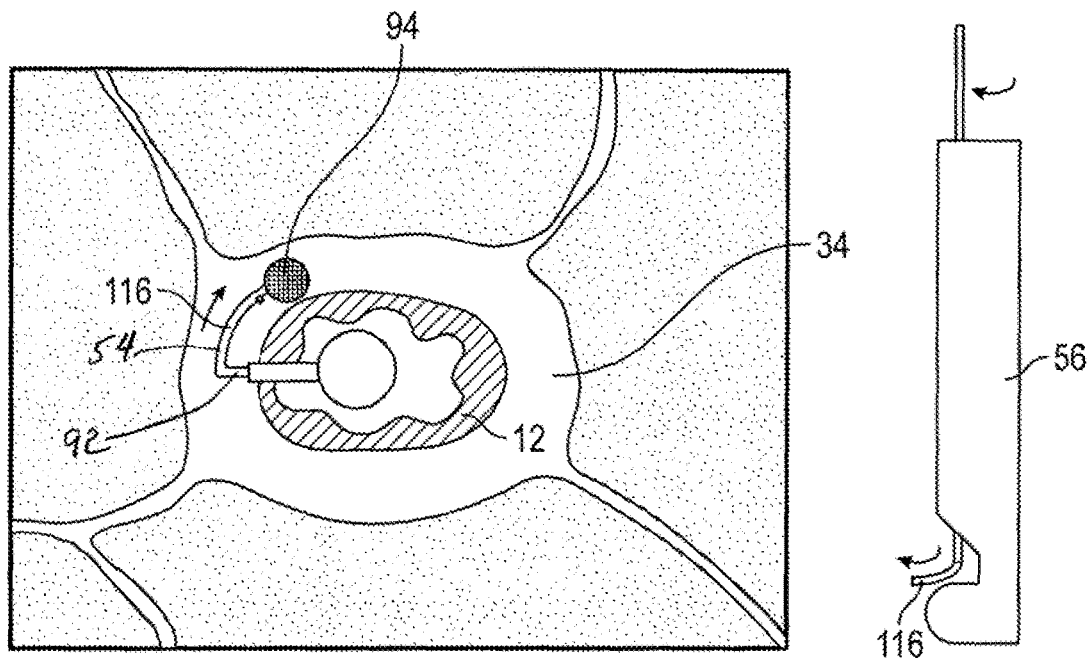
FIG. 9B is a schematic view of endoscopic device of FIG. 2, illustrating that as the operator controls the handle of the endoscope, they selectively and controllably (as the direction indicated by the arrow) move the curved portion of the guide member for guiding the distal end of the elongated deformable portion in a subfascial area.
Figures 10A, 10B:
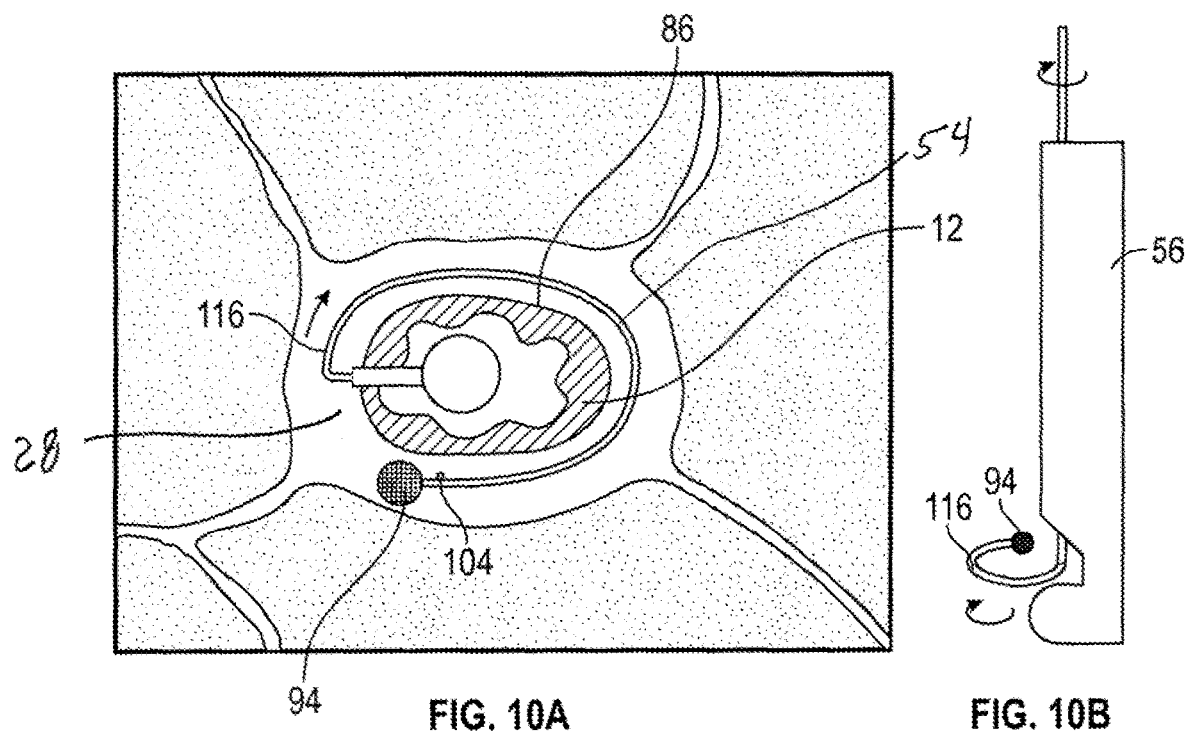
FIG. 10A is a schematic view of the neurostimulator assembly being placed in the subfascial area shown in FIG. 1C according to one embodiment, illustrating a joint-type guide member with a curved portion is advanced to guide the elongated deformable portion.
FIG. 10B is a schematic view of endoscopic device of FIG. 2, illustrating the operator can control the handle of the endoscope to selectively and controllably (as the direction indicated by the arrow) move the curved portion of the guide member to advance the distal end of the elongated deformable portion in a subfascial area to encircle partially or fully the esophagus.

FIG. 9A is a schematic view of the neurostimulator assembly being placed in the subfascial area shown in FIG. 1C according to one embodiment, illustrating a joint-type guide member in which a curved portion is formed as a connection (i.e. a joint) between the guide member 92 and the elongated deformable portion 54. FIG. 9B is a schematic view of endoscopic device of FIG. 2, illustrating the result of the operator controlling the handle of the endoscopic device to selectively and controllably (in the direction indicated by the arrow) move the curved portion of the guide member 92 for guiding the distal end of the elongated deformable portion 54 in a subfascial area 34. FIG. 10 A is a schematic view of the neurostimulator assembly 100 being placed in the subfascial 34 area shown in FIG. 1C according to one embodiment, illustrating a joint-type guide member 92 with a curved portion is advanced to guide the elongated deformable portion. FIG. 10B is a schematic view of endoscopic device of FIG. 2, illustrating the operator can control the handle of the endoscope to selectively and controllably (as the direction indicated by the arrow) move the curved portion of the guide member 92 to advance the distal end of the elongated deformable portion 54 in a subfascial area 34 to encircle partially or fully the esophagus 12. The guide member 92 can further form a curved portion provided at its distal end. The curved portion can be manufactured by any technologies known in the art, such as the hook-type or curved type flexible tip of an endoscopic retractor or the curved portion disclosed in the U.S. Pat. No. 8,868,215 B2, which is incorporated herein by reference in the entireties, except for any definitions, subject matter disclaimers or disavowals, and except to the extent that the incorporated material is inconsistent with the express disclosure herein, in which case the language in this disclosure controls. The curved portion has an interior bore (not shown) which allows guiding a distal end of the elongated deformable portion to advance or retract therein in response to the control action performed by the operator using the control handle of the endoscope 56. Thus, as shown in FIGS. 9A and 10A, the distal end of the elongated deformable portion 54 can be advanced within the curved portion to encircle partially or fully the esophagus 12. In addition, the elongated deformable portion 54 of FIGS. 10A and 10B can be configured as an implantable device as described above. Then, the modulation can be further performed on the targeted treatment area as described above.

Referring now to FIGS. 11 to 23, a further embodiment of an implantable member, and the deployment thereof to surround the outer wall of a body lumen such as the esophagus 12, are shown. Referring initially to FIGS. 11 to 14, the implantable member of this embodiment includes a pre-shaped implantable portion 204, which is deliverable from a delivery system 200, using a preshaped guidewire 202, to deliver the implantable portion 204 to a location surrounding or partially surrounding the outer wall 86 of the esophagus 12. The delivery system 200 also includes a first, inner, flexible tubular member 206 configured to receive the guidewire 202, and the implantable portion 204 located over a portion of the guidewire 202, within channels 208, 210 extending inwardly of the outer wall 212 thereof, and a second, outer, flexible tubular member 214 within which the first flexible tubular member 206 is deployable to be rotated with respect to the second, outer flexible tubular member 214, such that the distal end of the guidewire 202 and portions of the guidewire 202 spaced therefrom may be deployed outwardly of the second, outer flexible tubular member 214 through an opening 216 in the circumferential body 218 of the second, outer flexible tubular member 214. Once deployed, the deployed portion of the guidewire 202 forms a guide over which the implantable portion 204 is guided to be located around, or substantially around, the esophagus 12. When the guidewire 202 is retracted, the implantable portion remains around the esophagus, and because its shape is no longer restrained by the guidewire 202, it deforms to squeeze the esophagus 12 inwardly (FIG. 22).

Figure 11:
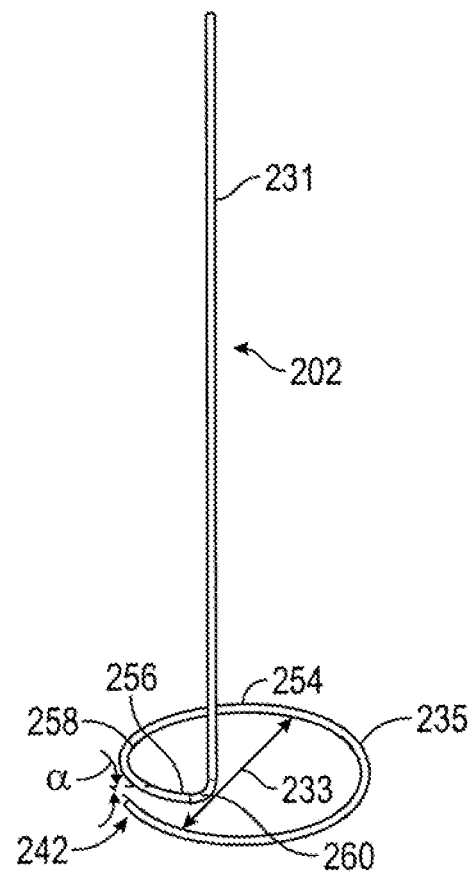
FIG. 11 is an isometric view of a preshaped guidewire useful for delivery of an implantable member to a location around the exterior of an esophagus or other body lumen.

As shown in FIG. 11, the pre-shaped guidewire 202 includes a first, generally straight portion 231 and a hoop portion 235 extending from the distal end of the straight portion 231. The straight portion 231 extends from the hoop portion 235 a distance sufficient, when deployed though a passage in an ultrasound endoscope 56, to extend to a location exterior of a patients mouth (not shown), plus at least the length of the hoop portion 235. The hoop portion 235 is configured of a shape memory material which regains its shape when released form a deforming restraint, such as the channel 210 in the delivery system 200. The straight portion 231 needs not be configured as a shape memory material, but can instead by a wire or a coil of a biocompatible material In an unconstrained state, the hoop portion 235 extends generally along the circumference of a circle, where the diameter 233 of the circle is greater than the greatest width between opposite sides of the esophagus 12 at the outer wall 86 thereof around which the hoop portion 235 is to be deployed.

Figure 12:
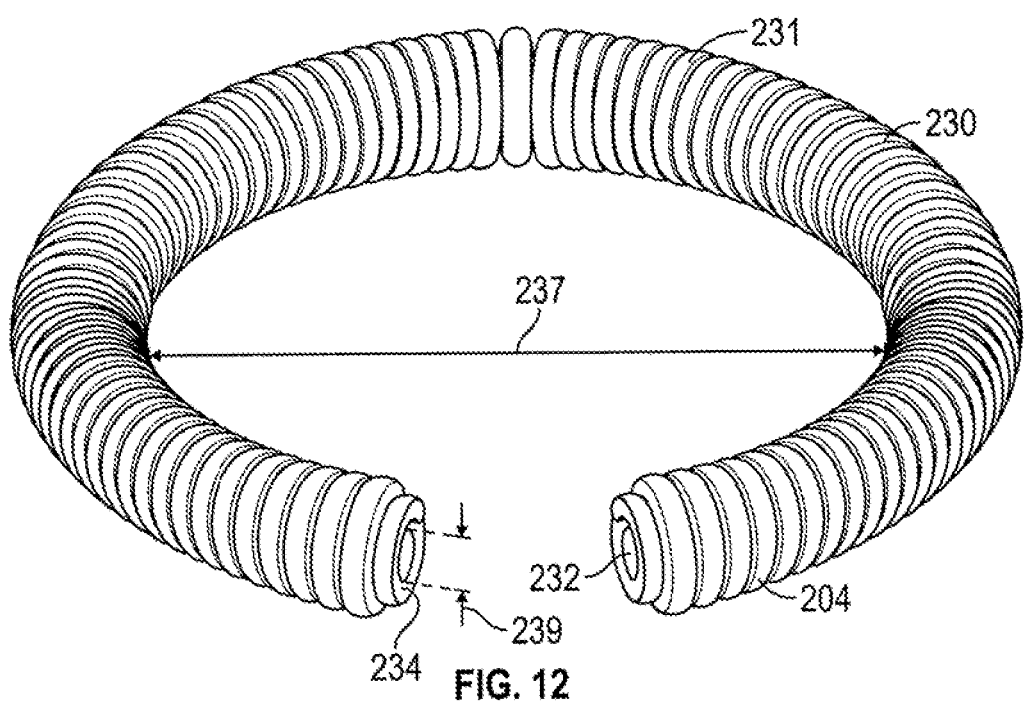
FIG. 12 is an isometric view of an implantable member.

Implantable portion 204 is configured as a coil or spring like member where a biocompatible shape memory material is wound as a coil around and longitudinally along a central axis, and the resulting coil is configured as a C-shaped 230 member as shown in FIG. 12. The inner diameter or span 237 of the C-shaped member 230, in an unrestrained state, is less than the smallest width between opposite sides of the esophagus 12 at the outer wall 86 thereof around which it is to be deployed.

Figure 18:
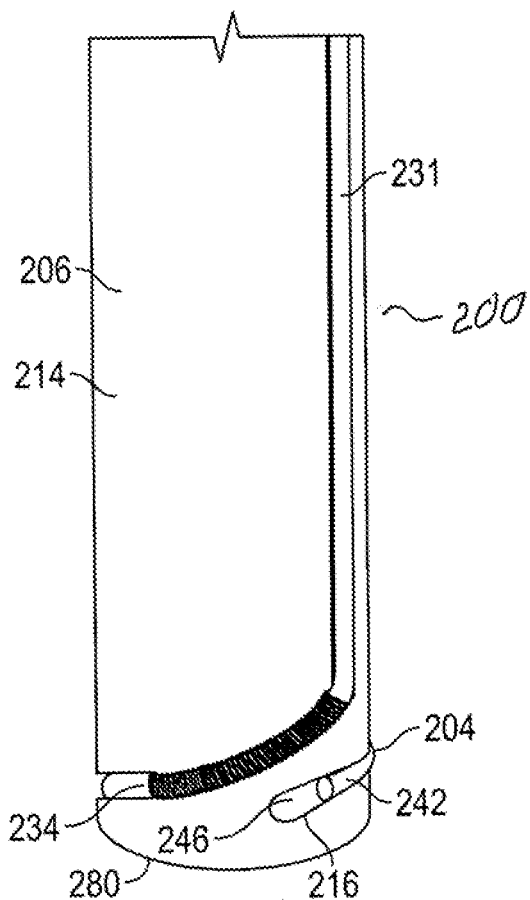
FIG. 18 is an isometric view of the delivery assembly, showing the second flexible tubular member in phantom.

To prepare for deployment of the implantable portion 204, the distal end 242 of the hoop portion 235 of the guidewire 202 is fed into the inner passage formed by the coil of shape memory material, initially at the second end 234 thereof, and the implantable portion 204 is pushed over the hoop portion 235, or the hoop portion 235 is pushed into the implantable portion 204, until the distal end thereof is directly adjacent to, or extends slightly outwardly of, the second end 234 of the hoop portion, as shown in FIG. 18, where the second flexible tubular member 214 is shown as transparent to show the disposition of the implantable portion 204 and guidewire 202 extending within the channel 210 of the first flexible tubular member 206 disposed therein. As the hoop portion 235 of the guidewire 202, in its free state, is greater in diameter (or circumference) than the circumferential channel 210, this can be accomplished by manually pressing the guidewire 202 with the implantable portion 204 located over the hoop portion 235 thereof into the channels 208, 210, and sliding the flexible tubular member 214 over the first flexible tubular member 206 to restrain the guidewire 202 in the channels 208, 210, wherein the distal end 242 of the hoop portion 235 of the guidewire 202 is disposed at, or slightly within, a blend portion 244 of the channel circumferential channel 210 at the passage thereof through the circumferential body 218 at the opening 216 therethrough. The base 246 of the opening 216 extending through the circumferential body 218 extends at a tangent "t" from the inner circumference (not shown) of the second flexible tubular member 214. As a result, as the guidewire 202 is extended outwardly of the opening 216, because the straight portion 231 of the guidewire 202 bears against the sidewall of channel 2168, it prevents the hoop portion 235 of the guidewire 202, but not the implantable portion 204 thereover, from retracting into the straight channel 208, and the base 246 of the opening 216 serves as a ramp tending to force the guidewire outwardly of the opening initially along the tangent t.

Figure 13:
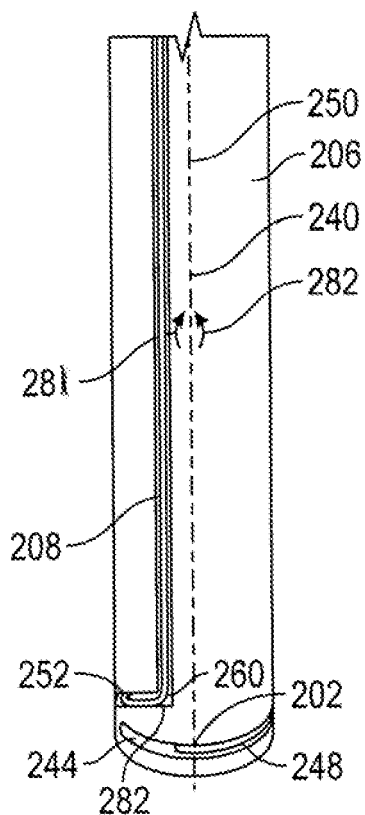
FIG. 13 is an isometric view of a first flexible tubular member useful for delivery of an implantable member to a location around the exterior of an esophagus or other body lumen, having the preshaped guidewire disposed in a series of channels therein.

Referring to FIG. 13, the configuration of the hoop portion 235, and the matching configuration of the circumferential channel 210 are shown. Here, the channel 210 includes a first circumferential portion 248 extending substantially around the first flexible tubular member 206 in a first plane generally perpendicular to the centerline 250 of the first flexible tubular member 206, and a second portion 252 extending more than 0°, and less than 90°, along the outer surface of the outer circumferential body 218 of the second flexible tubular member 214, in a second plane extending at an angle a of on the order of 10° to 40° with respect to the plane of the first circumferential portion 248.

Figure 14:
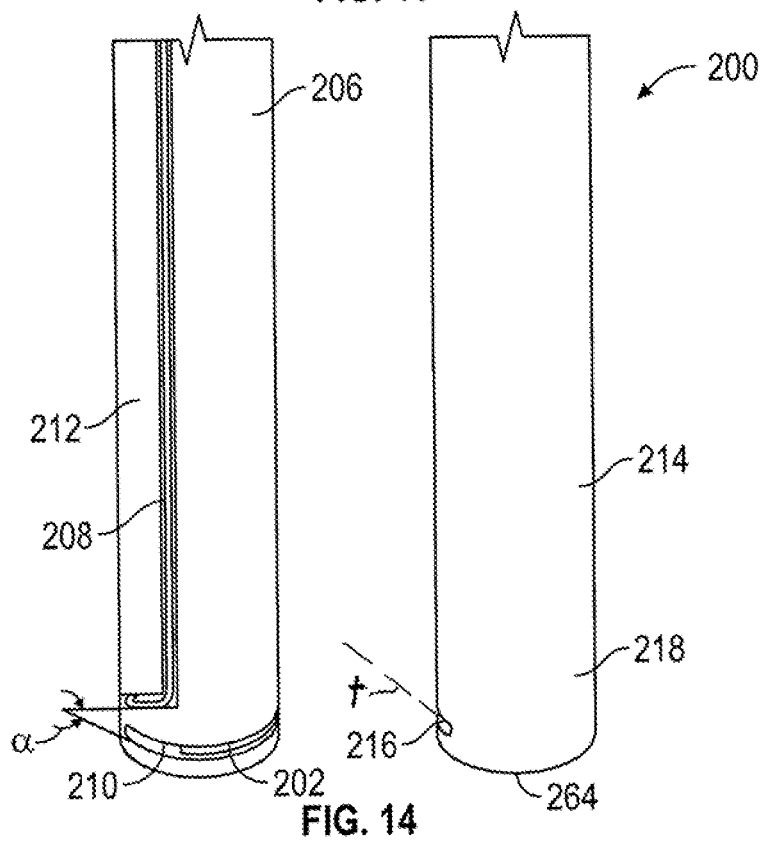
FIG. 14 is an isometric view of the first flexible tubular member having the preshaped guidewire disposed in a series of channels therein and a second flexible tubular member which is receivable over the first flexible tubular member and together forming a delivery assembly.

Likewise, as shown in FIG. 11, the hoop portion 235 of the guidewire 202 includes a first hoop portion 254 extending in a first plane about approximately the circumference of an imaginary circle, and a second hoop portion 256 extending in a second plane extending more than 0°, and less than 90° along the same imaginary circle as extends the first hoop portion 254, which are joined together at a first bend 258. A second end of the second hoop portion 256 joins the straight portion 237 at a second bend 260. The second plane extends at an angle a of on the order of 10° to 40° with respect to the plane of the first hoop portion 254. Additionally, as shown in FIG. 14, the distance between the first flexible tubular member distal end 262 and the circumferential channel 210 and the second flexible tubular member distal end 264 and the opening 216 are the same distance.

Figure 15:
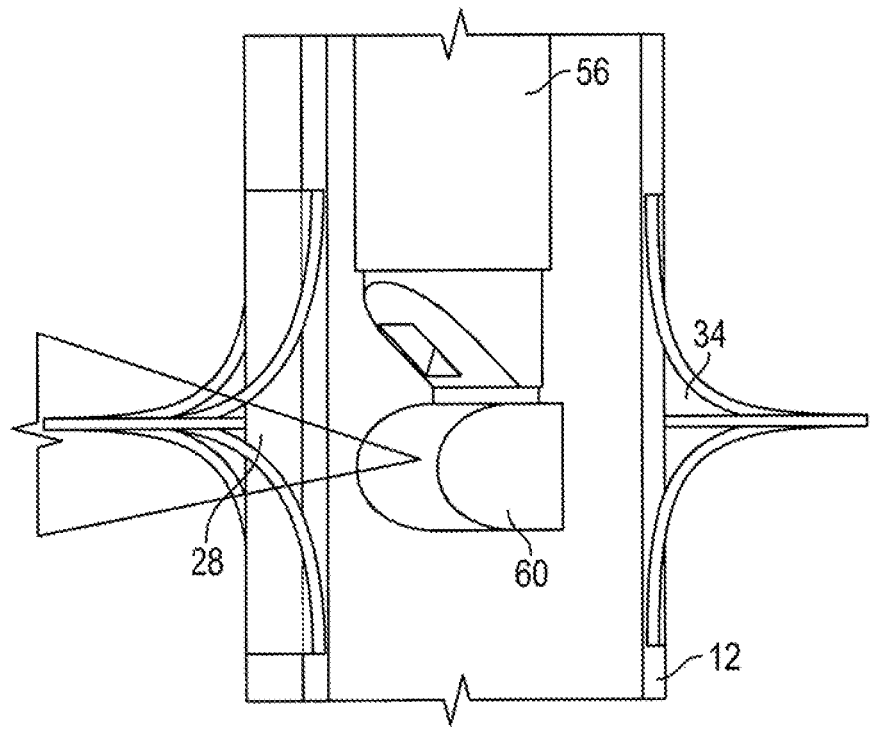
FIG. 15 is an isometric view of a portion of an esophagus, showing the terminal end of an endoscope deployed therein adjacent to the phrenoesophageal ligament.

Referring to FIG. 15, a location of a body lumen, for example the esophagus 12 and the subfascial area 34 surrounding the esophagus at the POL 28, are shown schematically in cutaway. In FIG. 15, an ultrasound endoscope 56 is inserted through the mouth or other opening of a patient, such that the distal end 60 thereof is deployed adjacent to the subfascial area 34 at the POL 28.

Figure 16:
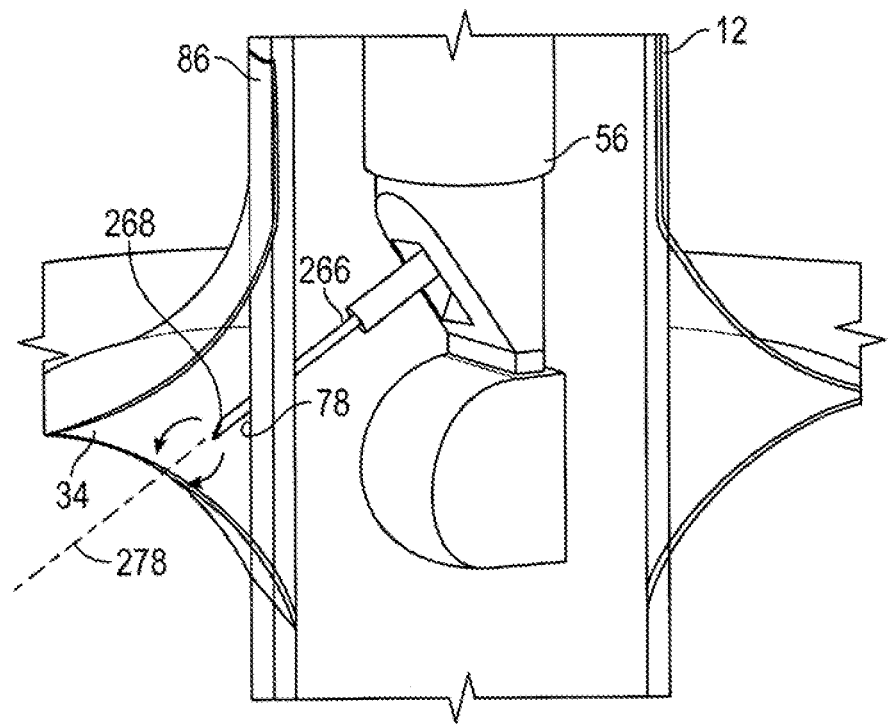
FIG. 16 is an isometric view of the portion of the esophagus of FIG. 15, showing a fine needle penetrating through the wall of the esophagus and into the subfascial region thereabout.

With the ultrasound endoscope 56 deployed as shown in FIG. 15, a fine needle 266 is extended therefrom, and through the circumferential surrounding body of the esophagus 12, such that the sharp end 268 of the needle 220 extends outwardly of the surface of the outer wall 86 of the esophagus 12 as is shown in FIG. 16 to form the connected channel 78. The subfascial area 34 is then dissected and dilated away from the outer wall 84 of the esophagus by the injection of saline into the subfascial area 34. The needle 266 may be rotated about its longitudinal axis 278 while the saline solution is injected into the subfascial area 34. Alternatively, in place of fine needle 266, an anchor 272 having a piercing tip 274 is extended toward the inner wall 54 of the esophagus 12, and rotated such that a threaded portion 276 extends through the wall of the esophagus 12 to form the connected channel 78 as shown in FIG. 17. Thence, as with fine needle 266, the subfascial area 34 is then dilated away from the outer wall 84 of the esophagus 12 by the injection of saline into the subfascial area 34. The anchor 272 may be rotated about its longitudinal axis 278 while the saline solution is injected into the subfascial area 34.

Figure 19:
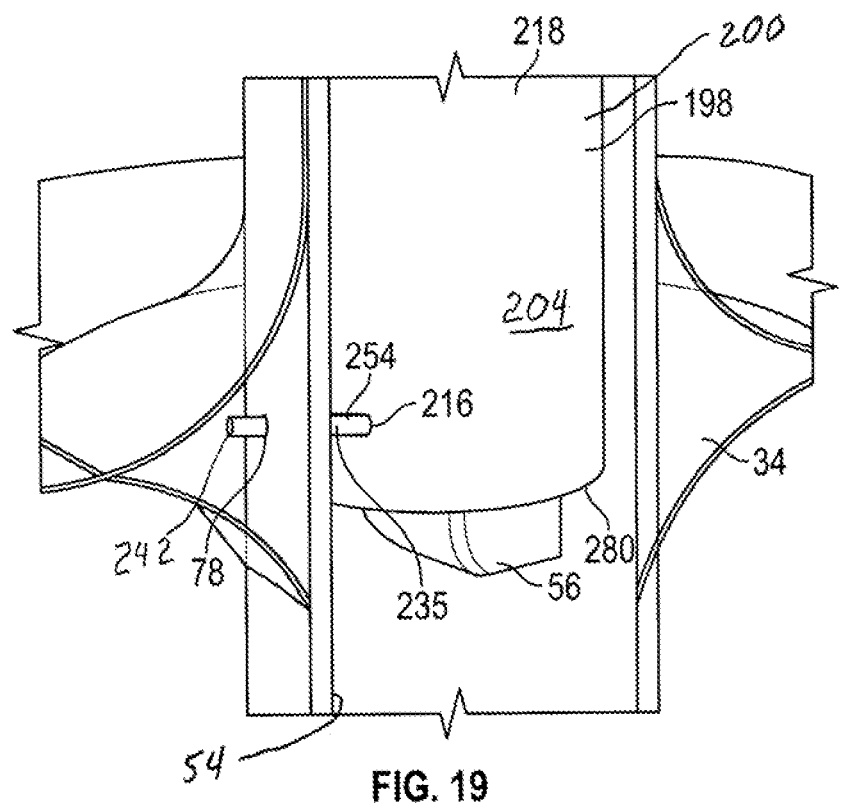
FIG. 19 is an isometric view of the delivery assembly, showing the guidewire extending through a connected channel through the esophagus wall and into the subfascial area.
Figure 20:
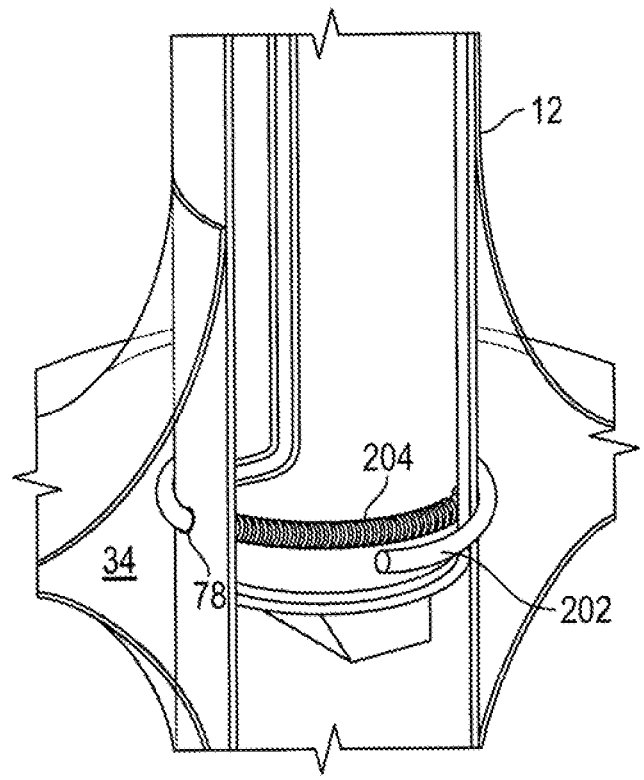
FIG. 20 an isometric view of the delivery assembly, showing the guidewire extending into the subfascial area and substantially around the esophagus.

Once the esophagus 12 has been pierced to form the connected channel 78 and the subfascial area 34 dilated, the fine needle 266 or anchor 272 is retracted, and the deployment assembly 200 substantially as shown in FIG. 18 (which shows the deployment assembly without the outer tube 204 for clarity) is fed over the flexible insertion tube 58 of the ultrasound endoscope 56 from a location outward of the patients mouth, such that the distal end 280 thereof is located such that the opening 216 thereof is located adjacent the elevation of the connected channel 78 (see, e.g. FIG. 23), and the tangent t of the opening 216 extends to the inner wall 54 of the esophagus 12 at, or closely adjacent to, the opening of the connected channel 78 therethrough (FIG. 19). Thence, the portion of the guidewire 202 extending outwardly of the patients mouth is pushed to push the distal end 242 of the first hoop portion 254 of the hoop portion 235 of the guidewire 202 toward, and through, the connected channel 78 as shown in FIG. 19, while the implantable member 204 remains within the channel 210, and begins backing inwardly of the channel 208. The entire delivery system 200 may also be rotated about the flexible insertion tube 58, as well as moved laterally thereon, to position the distal end 242 of the guidewire 202 to be inserted through the connected channel 78. The physician or other operator guiding the guidewire can use the camera 62 and a monitor adjacent to the working area exterior of the patient to visualize the locations of the connected channel 78 and distal end 242 of the guidewire 202 to effect the extending of the guidewire inwardly of the connected channel 78.

Once the distal end 242 of the guidewire 202 is extended through the connected channel 78, the physician or operator may extend the guidewire to extend the first hoop portion 254 around the outer surface of the esophagus 12 as shown in FIG. 20, where again the outer tube of the deployment assembly 200 is not shown for clarity of the deployment), which, when fully deployed, causes the implantable member 204 to fully back into the channel 208. To affect this deployment, the outer flexible tubular member 206 is rotated about the longitudinal axis 250 thereof in the forward rotation direction 281 (FIG. 13). Referring back to FIG. 13, at the guidewire 202, at the second bend 260 thereof, moves through a channel bend 282 connecting the channels 202, 210. By rotating the first tubular flexible member 206 in direction 281, the distal end 242 of the guidewire will likewise move in the same direction at the same angular rate of rotation because it cannot back into the channel 208 as it is restrained from doing so by engagement of the straight portion 231 against the sidewall of the channel 208. Any restriction on the movement of the distal end 242 causes the second hoop portion 254 to push the second bend 260 of the guidewire 202 against the lowermost end of the channel 202, causing rotation of the first flexible tubular portion 206 to cause rotation of the second bend 260 at the same angular rate of rotation and same direction. As the inner surface of the opening 216 along the tangent t maintains a fixed position if the operator maintains the outer tube 204 in a fixed position against rotation, the distal end 242 of the guidewire 202 moves further from the opening 216 and the opening 216 pushes on the portion of the guidewire 202 extending therethrough to cause the first flexible tubular member to move linearly within the second flexible tubular member, and the combination of such movements results in feeding of the first hoop portion 254 of the guidewire 202 outwardly of the opening, to cause the first hoop portion 254 to become deployed around, or substantially around, the outer surface 86 of the esophagus 12. The deployment of the first hoop portion 254 outwardly of the opening 216 is self-limited by the structure of the channels 208, 210 and the guidewire 202, as the straight portion 231 of the guidewire is insufficiently flexible to bend from its straight configuration to extend outwardly of the opening 216. Here, as the guidewire 202 is extended by rotating the first flexible tubular member 206, the second bend 260 of the channels becomes adjacent to the inner end of the opening, and as the guidewire at that location extends parallel to the longitudinal axis of the first flexible tubular member 206, the guidewire cannot further extend outwardly of the opening 216.

Figure 21:
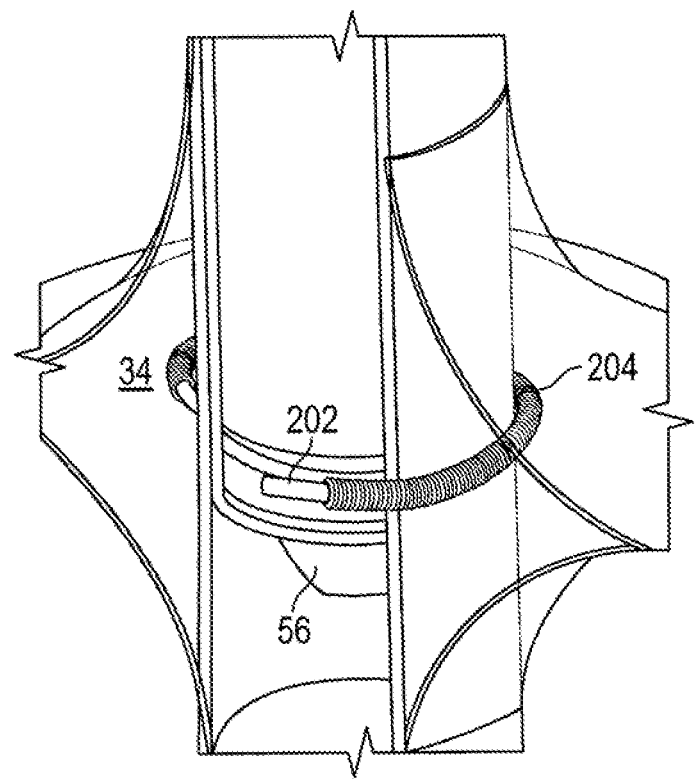
FIG. 21 an isometric view of the delivery assembly, showing the implantable member of FIG. 12 located on the guidewire and extending substantially around the esophagus.
Figure 22:
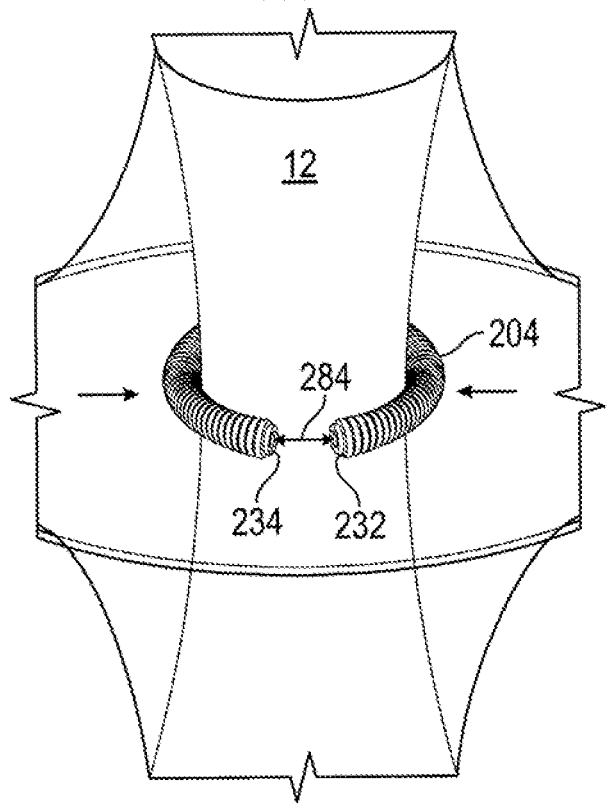
FIG. 22 an isometric view of the implantable member of FIG. 12 extending substantially around the esophagus in an unconstrained state.

At this point, the guidewire 202 can be partially retracted from the connected channel 78, such that a portion thereof is within the second portion 252 of the circumferential channel 210, and then the implantable portion 204 is pushed by a push tube (not shown) extended from an location external to the patients mouth and at the opposed end thereof against the second end 234 of the implantable member 204, pushing the first end 232 of the implantable member 204 outwardly of the channel 208 and into the circumferential channel 210, and thence outwardly of the opening 216 as is shown in FIG. 21. Once the implantable member 204 has been deployed in the subfascial area 34 and around the esophagus 12 as shown in FIG. 21, the guidewire 202 is retracted inwardly of the opening 216 in the deployment assembly, such as by rotating the first flexible tubular member 206 in the reverse direction 283 (FIG. 13) or by pulling it from a location exterior of the patient. Because the flank or side of the channel 208 will engage against the side of the straight portion 231 of the guidewire 202, rotation of the first flexible tubular member 206 in direction 283, while maintaining second flexible tubular member against rotation, will cause the guidewire 202 to retract inwardly of the opening leaving the implantable member 204 in place, as shown in FIG. 22, where the implantable member 204 is shown having regained its original unconstrained configuration to squeeze around the circumference of the outer wall 86 of the esophagus 12. Because the C shaped implantable member 204 can expand to increase the gap 284 between the first end 232 and second end 234 thereof, as material such as food or liquid passes through the esophagus 12, the outer wall 86 of the esophagus 12 will push outwardly to increase the length of the gap 284, but once this material has passed the location of the implantable member 204, it will spring back to its free shape to prevent material from leeching therepast in the opposite direction.

Alternatively, the wire of the second hoop portion 256 of the guidewire may be configured as thicker than the wire of the first hoop portion 254 of the hoop portion 235, wherein at least a portion of the second hoop portion 256 is wider than the inner diameter 239 of the implantable portion 204. Thus, as the first hoop portion 254 is being deployed around the esophagus 12, the implantable member is unable to retract along the second hoop portion 256, causing the implantable portion to deploy around the esophagus 12 at the same time the first hoop portion 254 is deployed around the esophagus. Thereafter, the guidewire 202 is retracted from the subfascial area 34, and the implantable member 204 remains in place as shown in FIG. 22.

Figure 23:
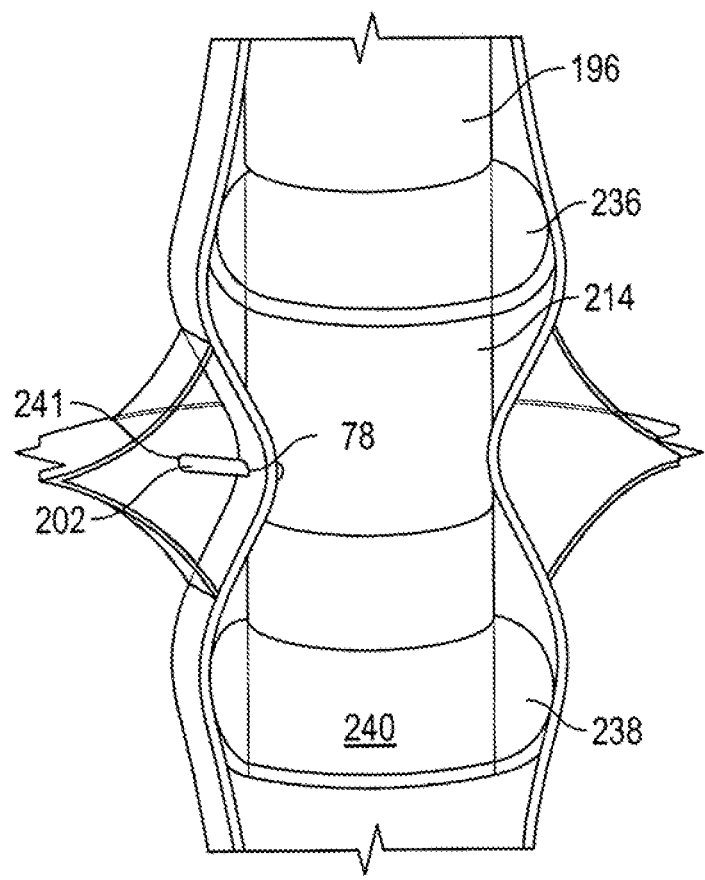
FIG. 23 is an is an isometric view of the delivery assembly, showing the second flexible tubular member in phantom, and supported within the esophagus by two separate balloons.

Referring to FIG. 23, the use of balloons 236, 238 to stabilize the position of the ultrasound endoscope 56 during deployment of the guidewire 202 is shown. Here, an upper balloon 236 is deployed about the deployment assembly 200 at a location above the connected channel, and a second balloon 238 is deployed around an extension 240 of the second flexible tubular member 214. The balloons may be deployed by suitable balloon catheters independently deployed, or by balloon catheters deployed through channels in the ultrasonic endoscope 56, or a combination of both.

It is to be noted that various modifications or alterations can be made to the above-described exemplary embodiments of the invention without departing from the technical features of the invention as defined in the appended claims.

What is claimed is:

1. A method for deploying a medical device, comprising:
   a) placing an endoscopic device endoluminally with respect to an esophagus of a patient to a first targeted site within the esophagus, wherein said endoscopic device includes:
      a flexible insertion tube having a proximal end and a distal end and configured for extending in a longitudinal direction and be inserted into a body lumen;
      an ultrasound transducer provided at the distal end and configured for emitting ultrasound and producing ultrasound data to navigate the distal end of the insertion tube to the first targeted site and;
      a first working channel provided at the distal end and configured for slidingly providing tool access and control;
   b) inserting a flexible, elongated member with a piercing part at the distal end thereof through the first working channel to the first targeted site;

c) creating a connected channel between an inner wall and an outer wall of the esophagus by perforating the inner wall at the first targeted site to the outer wall thereof with the piercing part;

d) introducing a neurostimulator assembly comprising a flexible sheath and a steerable guide member therein through the first working channel and the connected channel to the outer wall of the esophagus, wherein said guide member comprising:

an elongated deformable portion at a distal end of the guide member, and at least one modulator being deployed about an exterior surface of the elongated deformable portion; and e) at least partially encircling the esophagus of the patient with the modulator by advancing the elongated deformable portion of said guide member sub-fascially in a subfascial area from the outer wall of the esophagus.

2. The method of claim 1, wherein the endoscopic device of the step a) further comprises an imaging device or an illuminating device provided at the distal end.

3. The method of claim 1, wherein the endoscopic device of the step a) further comprises one or more additional working channels provided at the distal end.

4. The method of claim 1, wherein the first targeted site of the step b) is located at an esophagogastric junction, an esophageal-diaphragmatic junction, or an gastro-diaphragmatic junction.

5. The method of the claim 4, the step b) further comprises:

placing a balloon catheter having at least an inflatable balloon to the esophagogastric junction, and inflating the balloon to:
support the inner wall of the esophagus, and
maintain the elongated deformable portion at a predetermined position.

6. The method of claim 1, wherein the piercing part of the step b) comprises a needle or a cannula.

7. The method of claim 1, wherein the modulator of the step d) further comprises a device selected from the group consisting of monopolar electrodes, bipolar electrodes, quadrapolar electrodes, multipolar electrodes, optical stimulation devices, electromagnetic stimulation devices, radiofrequency stimulation devices, electrostatic stimulation devices, magnetic stimulation coils, vibratory stimulation devices, mechanical stimulation devices, acoustic stimulation devices, drug delivery catheters, chemical stimulation devices, electrolytic stimulation devices, thermal stimulation devices, neural stimulation devices, and neural inhibition devices.

8. The method of claim 1, wherein the guide member of the step d) further comprises a curved portion whereby a distal end of the elongated deformable portion is guided through the curved portion to encircle the esophagus.

9. The method of claim 1, wherein the guide member of the step d) further comprises an inflatable balloon area at the distal end of the guide member, whereby the subfascial area is dissected when the balloon area is inflated.

10. The method of claim 1, wherein the step e) further comprises applying a magnetic force to guide the elongated deformable portion of the guide member.

11. The method of claim 10, wherein the elongated deformable portion of the guide member further comprises a magnetic proximal end configured for guiding the distal end of the elongated deformable portion to encircle the esophagus.

12. The method of claim 1, wherein the modulator of the step e) is configured to perform modulation by applying a stimulation selected from mechanical, optical, electromagnetic, thermal, cold, electrical, magnetic, chemical, acoustic, pharmaceutical stimulation or the combination thereof.

13. The method of claim 1, wherein the at least partially encircling the esophagus includes encircling a vagal nerve, a diaphragmatic muscle, a splanchnic nerve or a celiac ganglia.

* * * * *